United States Patent [19]

Subsara et al.

[11] Patent Number: 4,543,175
[45] Date of Patent: Sep. 24, 1985

[54] ION RESPONSIVE PROBE

[75] Inventors: William P. Subsara, Santa Ana; Michael R. Levonius, Anaheim, both of Calif.

[73] Assignee: Gam Rad, Inc., Garden Grove, Calif.

[21] Appl. No.: 521,178

[22] Filed: Aug. 8, 1983

[51] Int. Cl.[4] .................. G01N 27/46; G01N 27/28
[52] U.S. Cl. .................. 204/400; 204/435; 204/286
[58] Field of Search .......... 204/400, 415, 435, 418, 204/419, 286, 297 R

[56] References Cited

U.S. PATENT DOCUMENTS

| | | | |
|---|---|---|---|
| 3,103,480 | 9/1963 | Watanabe et al. | 204/420 |
| 3,202,596 | 8/1965 | Canevari | 204/197 |
| 3,239,444 | 3/1966 | Heldenbrand | 204/415 |
| 3,454,485 | 7/1969 | Hauk et al. | 204/415 |
| 3,503,861 | 3/1970 | Volpe | 204/415 |
| 3,526,577 | 9/1970 | Molloy | 204/415 |
| 3,607,710 | 9/1971 | Farren | 204/419 |
| 3,764,504 | 10/1973 | Arff et al. | 204/415 |
| 3,932,233 | 1/1976 | Ruzicka et al. | 204/418 |
| 4,116,796 | 9/1978 | Havas et al. | 204/419 |
| 4,128,468 | 12/1978 | Bukamier | 204/435 |
| 4,133,732 | 1/1979 | Boeke | 204/419 |
| 4,166,020 | 8/1979 | Trampert | 204/435 |
| 4,218,299 | 8/1980 | Lindell et al. | 204/435 |
| 4,252,124 | 2/1981 | Maurer et al. | 204/435 |
| 4,255,244 | 3/1981 | Matsuyama et al. | 204/435 |

Primary Examiner—T. Tung
Attorney, Agent, or Firm—Harness, Dickey & Pierce

[57] ABSTRACT

An oxidation reduction potential probe having a chemically resistant plastic outer housing and an electrode located within the outer housing which includes a platinum band supported on a necked down portion of a chemically resistant plastic tube with a silver lead wire electrically connected to the platinum band, the necked down portion of the plastic tube and the platinum band extending out from the outer housing for immersion in a fluid to be measured.

6 Claims, 2 Drawing Figures

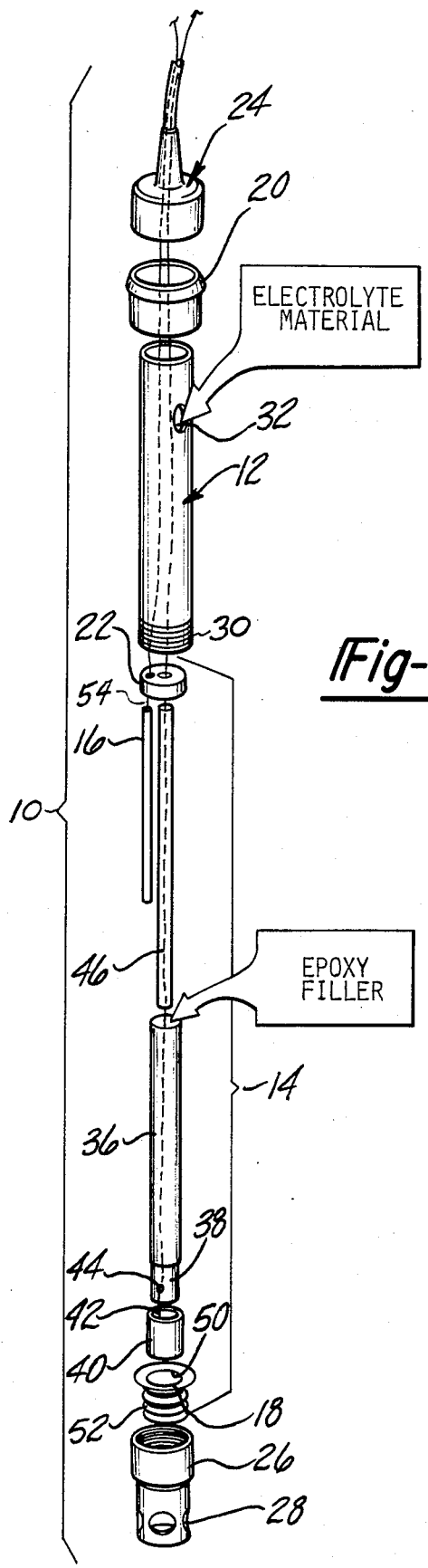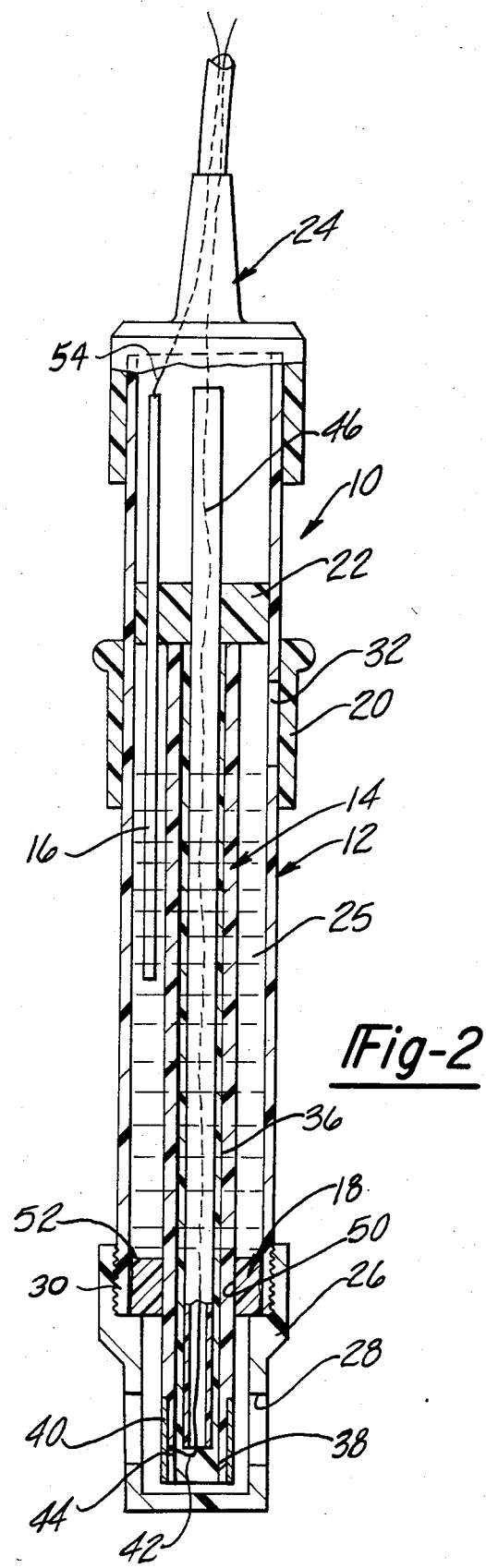

ION RESPONSIVE PROBE

BACKGROUND—SUMMARY OF THE INVENTION

The present invention relates to probes for use as sensors to detect selective ionic characteristics in a liquid solution and more particularly to a probe for use in detecting the oxidation and/or reduction potential of ions in such a solution.

In the past it has been common to construct probes using glass housings. With probes designed to detect the oxidation reduction potential of a solution (referred to as ORP probes), and electrode was formed using a platinum band bonded to a glass tube. Platinum was used because of its desirable conductivity characterstics and because of its resistance to various chemicals i.e. such as to HF, hydrofluoric acid. The platinum band typically was bonded to the glass tube during firing. Thus a straight hollow glass tube was fired to provide a necked down portion on which the platinum band was secured during the firing step. The result was a good, fluid tight bond. The platinum band was connected to a lead wire of platinum which was fed through an opening in the neck of the hollow galss tube for connection to a meter. At some location the platinum wire was connected by spot welding to a silver wire which completed the electrical circuit to the meter. Because of the heat generated in firing the glass tube to form the necked down portion the welded connection to the silver wire was located a considerable distance from the platinum band. This inherently required a substantial length of expensive platinum wire. At the same time the glass probe was susceptible to breakage in shipment and in use and hence was not adapted for rugged use or handling. Also the glass housing construction provided a reduced life for the electrode when used in solutions such as hydrofluoric acid and (HF) which attack and/or dissolve glass.

In the present invention as epoxy type plastic tube is used in place of the glass tube in a construction which obviates the problems of the prior construction and results in a rugged less expensive construction.

Other objects, features, and advantages of the present invention will become apparent from the subsequent description and the appended claims, taken in conjunction with the accompanying drawings, in which:

FIG. 1 is an elevational, sectional view of an assembled probe embodying features of the present invention; and FIG. 2 is an exploded view to reduced scale of the assembly of FIG. 1.

Looking now to FIG. 1 a combination oxidation reduction potential (ORP) probe is indicated by the numeral 10 and comprises a tubular outer body 12, an ORP electrode 14, a reference electrode 16, a porous junction 18, a refill sleeve 20, a cap 22, and a cable assembly 24. The outer body 12 is filled with a reference electrolyte 25 (not shown in FIG. 1) which can be gelled or in a liquid form having a preselected viscosity. A spinoff cap 26, having windows 28, can be threadably, removably secured to the immersible end of the outer body 12 to provide added protection for the exposed end of the ORP electrode 14. In operation the lower end of the probe 10 is immersed in a solution to be measured and the cable assembly 24 connected to a suitable meter (not shown) whereby an indication of the magnitude of the oxidation reduction potential of the solution can be obtained. In some cases the spinoff cap 26 may be used only for shipping and will be removed when the probe 10 is placed in use.

Looking now to FIGS. 1 and 2, the outer body 12 is a hollow tube and can be of a known construction of durable epoxy type plastic material which has good chemical resistance. The lower, outer end 30 of the body 12 is threaded whereby the windowed spinoff cap 26 can be threadably applied or removed. A refill opening 32 is located near the upper end of the tubular body 12 to facilitate filling and refilling with electrolyte 25. The refill sleeve 20 is of an elastomeric material and normally overengages and seals the refill opening 32 but can be selectively moved whereby access to the opening 32 can be had.

The ORP electrode 14 includes a hollow, tubular shank 36 which terminates in a reduced diameter tip 38. The outside diameter of shank 36 is considerably less than the inside diameter of the tubular body 12.

A band 40 is constructed of a material which is a good electrical conductor and which is resistant to highly active chemicals, such as HF, etc. Thus ring 40 is preferably made of platinum (although gold would also be suitable). A silver lead wire 42 is mechanically and electrically connected to the platinum band 40 and extends through a lead wire hole 44 located in the reduced diameter tip 38. The silver wire 42 can be spot welded to the band 40. Alternatively a short length of platinum wire could be connected to the band 40 and then connected to a silver lead wire. Thus since no firing takes place the length of platinum lead wire can be reduced or eliminated in comparison to prior constructions.

The band 40 is dimensioned to fit snugly onto the tip 38. The tubular shank 36 is also constructed of a durable plastic such as an epoxy type material having good chemical resistance. Thus the band 40 in being assembled to the tip 38 has an epoxy adhesive applied thereto to provide a good mechanical bond. An insulation tube 46 is of an outside diameter to be partially telescoped within the tubular shank 36. The silver lead wire extends through the insulation tube 46 and hence will not be in contact with the electrolyte 25. In order to assure a good seal the space between the tubular shank 36 and the insulation tube 46 is filled with epoxy cement. This seals the inside of the shank 36 from the solution being measured and from the electrolyte 25. In order to permit a good seal via the cement a sufficient clearance is desired between the outside diameter of the insulation tube 46 and the inside diameter of the tubular shank 36. In one instance the adequate clearance was provided where the outside diameter of the insulation tube 46 was 0.140" and the inside diameter of the tubular shank 36 was 0.250". This assembly defines the ORP electrode 14.

The electrode 14 is generally centrally located within the tubular outer body 12 and is supported at the lower end thereof in an annular ring or junction 18. The ring 18 is of a porous construction permitting ion exchange between the electrolyte 25 and the solution being measured. It has been found desirable in one form of the invention to utilize a porous junction 18 constructed of a fluorocarbon polymer such as Teflon i.e. polytetrafluoroethylene. Teflon is a trademark of DuPont, Inc. The outside surface of the annular junction 18 is sealingly received within the inside diameter of the tubular outer body 12 and also sealingly receives the tubular shank 36 in a central opening 50. The outside surface of the junction 18 can be provided with a plurality of annular sealing lips or ridges 52.

The reference electrode 16 can be of a well known type such as calomel. A calomel reference electrode consists of a small diameter glass tube, the upper and lower internal portions of which are separated by a glass plug which has a platinum wire bonded to and passed through it. The part of the platinum wire protruding into the lower portion of the tube makes contact with a layer of mercurous chloride (calomel) which is covered with a mixture of mercurous chloride (calomel) and liquid mercury which is in turn covered with a pool of liquid mercury. A packing plug of cotton separates the lower internal portion of the reference electrode 16 from the electrolyte 25. The platinum wire which protrudes from the upper portion of the reference tube is induction soldered to an electrical conductor 54 which has good conductive properties such as silver. Alternatively, a solid silver wire coated with silver chloride could be used as the reference electrode.

The cap 22 closes the upper end of the tubular outer body 12 and the cable assembly 24 connects the ORP electrode conductor 24 and the reference conductor 54 to a suitable meter (not shown).

The probe 10 is of a combination type wherein it includes both the ORP electrode 14 and the reference electrode 16. It should be noted that the details of the invention would also be applicable to a probe in which the reference electrode 16 was omitted from the probe 10 and a separate reference probe was used.

Thus the probe as shown and described is of a durable construction and by eliminating the need for exotic, expensive metals provides a relatively low cost construction.

While it will be apparent that the preferred embodiments of the invention disclosed are well calculated to fulfill the objects above stated, it will be appreciated that the invention is susceptible to modification, variation and change without departing from the proper scope or fair meaning of the invention.

What is claimed is:

1. An ion sensing probe for measuring the ionic characteristics of a liquid solution comprising: a tubular outer housing constructed of an epoxy plastic, a first electrode located within said outer housing and extending partially beyond one end of said outer housing, said first electrode including a tubular member constructed of an epoxy plastic and having a generally uniform outside diameter terminating at one end in a necked down portion having a reduced outside diameter, an annular platinum band located about said necked down portion, said platinum band having an installed outside diameter substantially the same as said uniform outside diameter whereby a generally continuous outer surface is provided by said platinum band and the adjacent portion of said tubular member, a first lead wire which is substantially silver connected to said platinum band and extending into said tubular member via an opening in said necked down portion, an insulating tube constructed of an epoxy plastic and located in clearance relationship within said tubular member and extending from substantially said necked down portion to a position outwardly of the opposite end of said tubular member, said first lead wire extending through said insulating tube and outwardly therefrom, the space between said insulating tube and said tubular member being filled with an epoxy plastic at least in the area of said necked down portion to seal the interior of said insulating tube from the solution being measured, a porous junction of polytetrafluoroethylene sealingly located at said one end of said outer housing, said tubular member of said first electrode sealingly located in an opening in said porous junction with said platinum band located beyond said one end of said outer housing, a reference electrode located within said outer housing, said outer housing filled with an electrolyte to at least partially immerse said reference electrode.

2. An ion sensing probe for measuring the ionic characteristics of a liquid solution comprising: a tubular outer housing constructed of a chemically resistant plastic, an electrode located within said outer housing and extending partially beyond one end of said outer housing, said electrode including a tubular member constructed of a chemically resistant plastic, an annular band of platinum located on a first end of said tubular member and secured thereto via an adhesive, a lead wire which is substantially of an electrically conductive material different from that of said band and extending into said tubular member to substantially the location of said band, means electrically connecting said lead wire to said band, means for sealing said tubular member from the liquid solution at least in the area of said band, an annular porous junction sealingly located at said one end of said outer housing, said tubular member sealingly located in an opening in said porous junction with said band located beyond said one end of said outer housing.

3. The probe of claim 2 with said first end of said tubular member being necked down to receive said band, said band having an outside diameter generally the same as that of said tubular member adjacent said necked down first and whereby a generally continuous outer surface is provided by said band and the adjacent portion of said tubular member.

4. The probe of claim 2 with said electrode including an insulating tube constructed of a chemically resistant plastic and located in clearance relationship with said tubular member and with said lead wire extending through said insulating tube, said sealing means sealing in the clearance between said tubular member and said insulating tube and the opening of said insulating tube at said first end of said tubular member.

5. An oxidation reduction potential probe for measuring the ionic characteristics of a liquid solution comprising: a tubular outer housing constructed of a chemically resistant plastic, an electrode located within said outer housing and extending partially beyond one end of said outer housing, said electrode including a tubular member constructed of a chemically resistant plastic and terminating at one end in a necked down portion, an annular band of platinum located on said necked down portion, said band having an outside diameter generally the same as that of said tubular member adjacent said necked down portion whereby a generally continuous outer surface is provided by said band and the adjacent portion of said tubular member, a lead wire which is substantially of an electrically conductive material different from that of said band and extending into said tubular member to substantially the location of said band, means electrically connecting said lead wire to said band, an insulating tube constructed of a chemically resistant plastic located in clearance relationship within said tubular member and extending from substantially said necked down portion to a position outwardly of the opposite end of said tubular member, said lead wire extending through said insulating tube and outwardly therefrom, the space between said insulating tube and said tubular member being filled with a chemically resistant plastic at least in the area of said necked down portion to seal the interior of said insulating tube from the solution being measured, an annular porous junction sealingly located at said one end of said outer housing, said tubular member sealingly located in an opening in said porous junction with said band located beyond said one end of said outer housing.

6. The probe of claim 5 with said space between said insulating tube and said tubular member being defined where the outside diameter of said insulating tube is around 0.140″ and the inside diameter of said tubular member is around 0.250″.

* * * * *